(12) United States Patent
Reimels

(10) Patent No.: US 12,064,100 B2
(45) Date of Patent: *Aug. 20, 2024

(54) SYSTEMS AND METHODS FOR TISSUE RETRACTION

(71) Applicant: Alphatec Spine, Inc., Carlsbad, CA (US)

(72) Inventor: William Reimels, Hamilton, OH (US)

(73) Assignee: Alphatec Spine, Inc., Carlsbad, CA (US)

( * ) Notice: Subject to any disclaimer, the term of this patent is extended or adjusted under 35 U.S.C. 154(b) by 141 days.

This patent is subject to a terminal disclaimer.

(21) Appl. No.: 17/748,364

(22) Filed: May 19, 2022

(65) Prior Publication Data

US 2022/0273283 A1 Sep. 1, 2022

Related U.S. Application Data

(63) Continuation of application No. 14/253,619, filed on Apr. 15, 2014, now Pat. No. 11,357,493.

(60) Provisional application No. 61/812,912, filed on Apr. 17, 2013.

(51) Int. Cl.
*A61B 17/02* (2006.01)

(52) U.S. Cl.
CPC ...... *A61B 17/0293* (2013.01); *A61B 17/0218* (2013.01)

(58) Field of Classification Search
CPC .................. A61B 17/0293; A61B 17/0218
USPC ................................ 600/201-245
See application file for complete search history.

(56) References Cited

U.S. PATENT DOCUMENTS

| | | | |
|---|---|---|---|
| 2012/0323080 A1* | 12/2012 | DeRidder | A61B 17/0218 600/215 |
| 2014/0074170 A1* | 3/2014 | Mertens | A61F 2/4611 606/279 |

* cited by examiner

*Primary Examiner* — Eduardo C Robert
*Assistant Examiner* — Tara Rose E Carter
(74) *Attorney, Agent, or Firm* — Robert Winn

(57) ABSTRACT

A system for interchangeable retractor blades includes a shell, a first retractor blade, and a second retractor blade. The shell includes a rigid proximal end configured to attach to a surgical retractor and an opening, a distal closed end, and a pliable portion including a pocket in communication with the opening and extending along a length of the shell to the distal closed end. The first retractor blade includes a first geometry received through the opening into the pocket and that shapes the pliable portion to configure the shell in a first configuration. The second retractor blade includes a second geometry received through the opening into the pocket and that shapes the pliable portion to configure the shell in a second configuration.

20 Claims, 9 Drawing Sheets

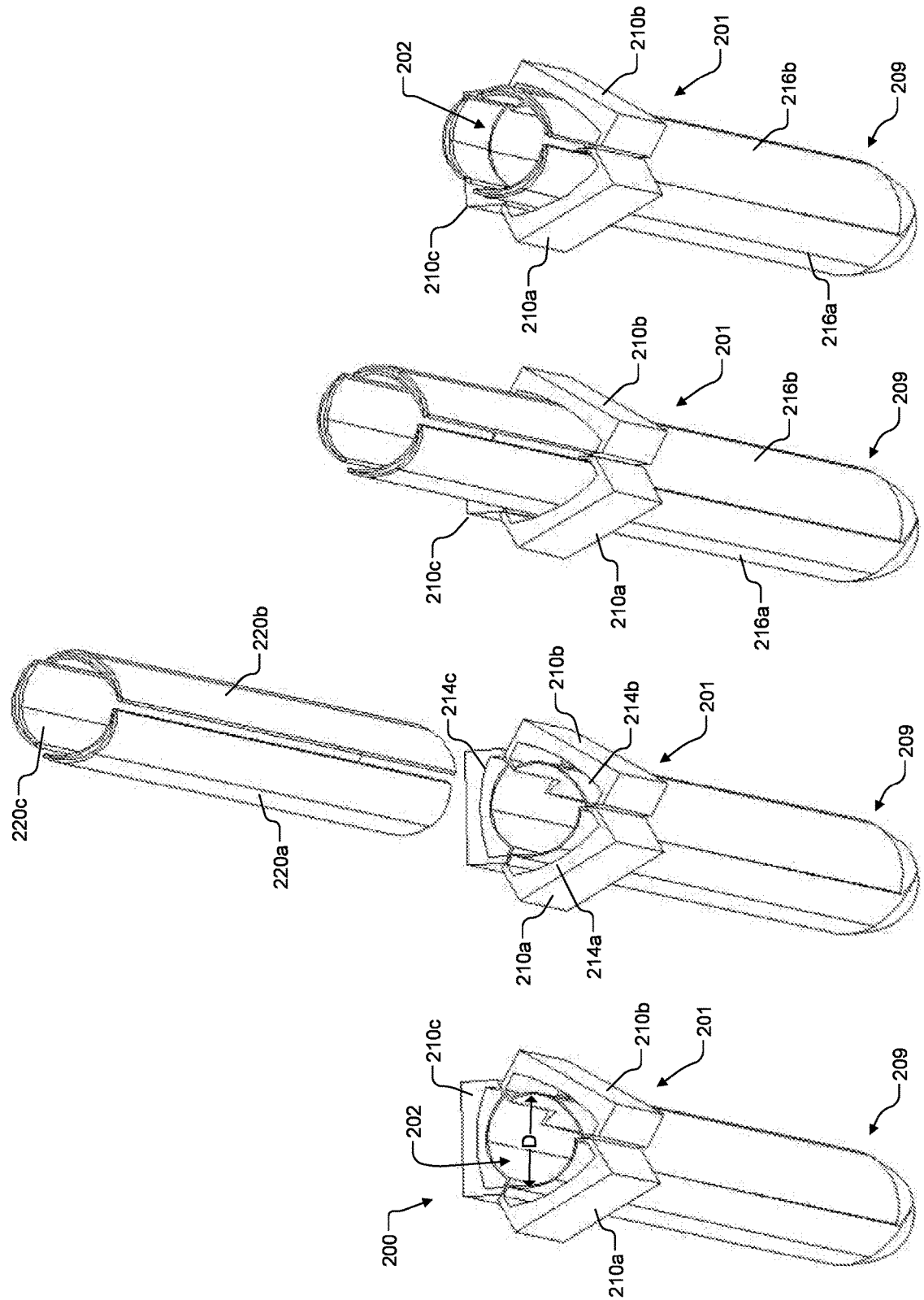

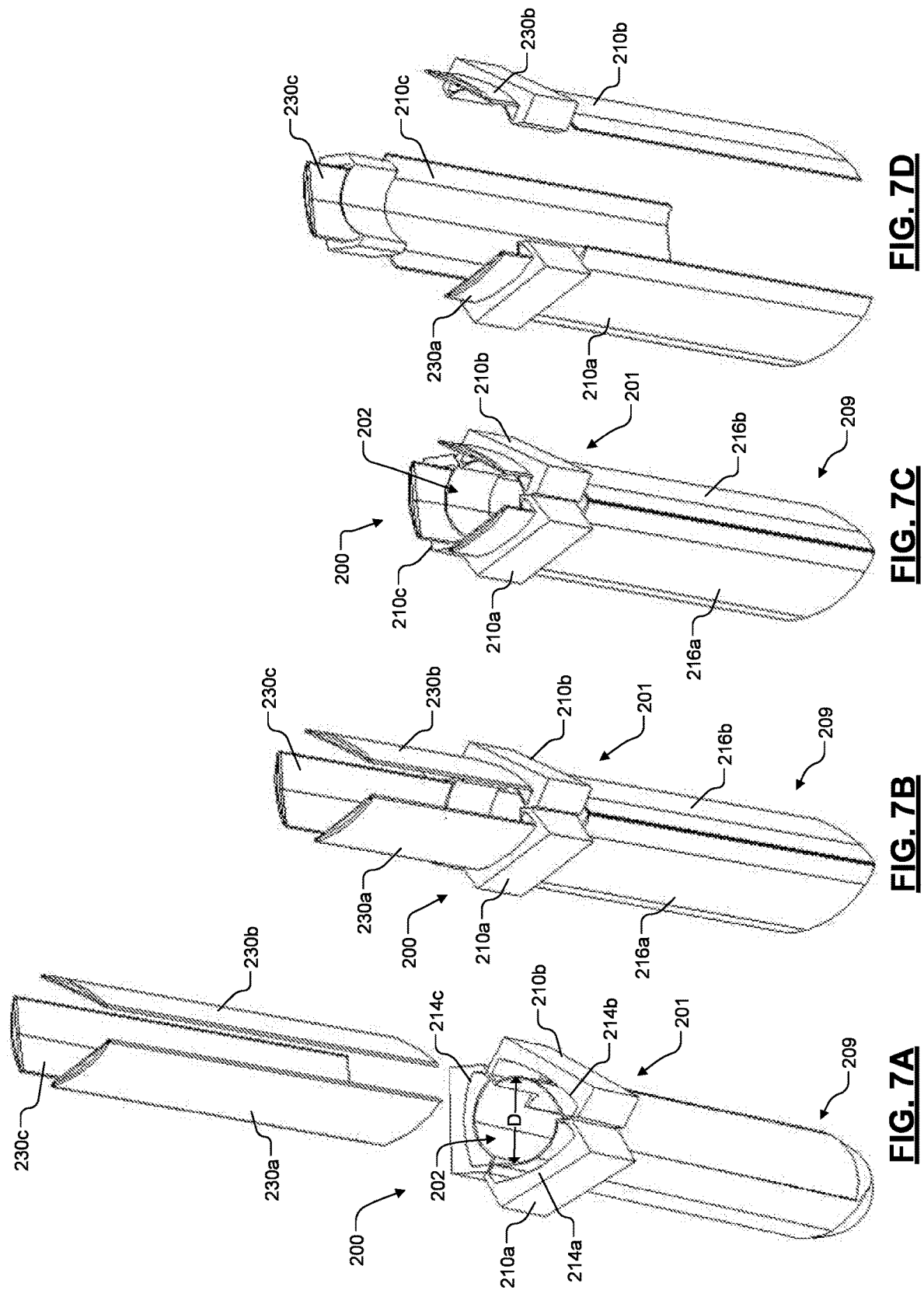

SYSTEMS AND METHODS FOR TISSUE RETRACTION

CROSS-REFERENCE TO RELATED APPLICATIONS

The present application is a continuation of U.S. application Ser. No. 14/253,619 entitled "Systems and Methods for Tissue Retraction" which was filed on Apr. 15, 2014 that claims priority to U.S. Provisional Application Ser. No. 61/812,912 entitled "Systems and Methods for Tissue Retraction" which was filed on Apr. 17, 2013 each of which is incorporated herein by reference in their entireties.

FIELD

The present disclosure generally relates to the field of spinal orthopedics, and more particularly to systems and method for retracting soft tissue of a surgical area.

BACKGROUND

The spine is a flexible column formed of a plurality of bones called vertebrae. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies. Various spinal disorders may cause the spine to become misaligned, curved, and/or twisted or result in fractured and/or compressed vertebrae. It is often necessary to surgically correct these spinal disorders.

The spine includes seven cervical (neck) vertebrae, twelve thoracic (chest) vertebrae, five lumbar (lower back) vertebrae, and the fused vertebrae in the sacrum and coccyx that help to form the hip region. While the shapes of individual vertebrae differ among these regions, each is essentially a short hollow shaft containing the bundle of nerves known as the spinal cord. Individual nerves, such as those carrying messages to the arms or legs, enter and exit the spinal cord through gaps between vertebrae.

The spinal disks act as shock absorbers, cushioning the spine, and preventing individual bones from contacting each other. Disks also help to hold the vertebrae together. The weight of the upper body is transferred through the spine to the hips and the legs. The spine is held upright through the work of the back muscles, which are attached to the vertebrae. While the normal spine has no side-to-side curve, it does have a series of front-to-back curves, giving it a gentle "S" shape. If the proper shaping, alignment, and/or curvature are not present due to scoliosis, neuromuscular disease, degenerative discs, tumors, trauma, or other disorder, it may be necessary to straighten or adjust the spine into a proper alignment and/or curvature.

Generally the correct curvature is obtained by manipulating the vertebrae into their proper position and securing that position with interbody spacers and a rigid system of screws and rods. In some instances, plates may secure the construct. Soft tissue retractor systems are used to provide direct access to the intervertebral space for disc extraction and interbody deliver. Generally, direct lateral approaches include insertion of a retractor system with three or more robust blades to split the psoas muscle and expand the retractor to pull away soft tissue from the surgical area to enable access by the surgeon.

One issue during expansion of the retractor is soft tissue encroachment between the opened blades. Other issues may relate to the ease with which the retractor expands the surgical area, especially in lateral surgeries where torque forces acting on distal ends of the blades may be significant. Complicated retractors lead to longer cleaning and sterilization times.

SUMMARY

A system for interchangeable retractor blades includes a shell, a first retractor blade, and a second retractor blade. The shell includes a rigid proximal end configured to attach to a surgical retractor and an opening, a distal closed end, and a pliable portion including a pocket in communication with the opening and extending along a length of the shell to the distal closed end. The first retractor blade includes a first geometry received through the opening into the pocket and that shapes the pliable portion to configure the shell in a first configuration. The second retractor blade includes a second geometry received through the opening into the pocket and that shapes the pliable portion to configure the shell in a second configuration.

In other features, the first geometry includes a first radius curvature in a plane normal to the length of the shell. The second geometry includes a second radius of curvature in the plane normal to the length of the shell that is greater than the first radius of curvature. The first retractor blade includes length commensurate with the length of the shell, overall thickness configured to slidably engage with the pocket, and a curved profile commensurate with a curvature of the shell in a plane normal to the length. The second retractor blade includes length commensurate with the length of the shell, overall thickness configured to slidably engage with the pocket, and a straight profile configured to decrease the curvature of the shell in the plane normal to the length.

A system for retracting tissue from a surgical area includes a retractor, a plurality of shells, a first plurality of blades, and a second plurality of blades. The retractor includes an actuator that positions a plurality of armatures. Each of the plurality of shells includes a rigid proximal end attached to each of the plurality of armatures and an opening, a distal closed end, and a pliable portion including a pocket in communication with the opening and extending along a length of the shell to the distal closed end. Each of the first plurality of retractor blades includes a first geometry received through the opening into the pocket and that shapes the pliable portion to configure the shells in a first configuration. Each of the second plurality of retractor blades includes a second geometry received through the opening into the pocket and that shapes the pliable portion to configure the shells in a second configuration.

In other features, the first geometry includes a first radius curvature in a plane normal to the length of the shell and the second configuration includes a second radius of curvature in the plane normal to the length of the shell that is greater than the first radius of curvature. The shells receive the first plurality of blades and the actuator positions the shells in a first position enclosing a first viewing area with a circular area of a first diameter.

In other features, the actuator positions the shells to a second position forming a second viewing area encompassed by the shells and planes extending from edges of adjacent shells, the second viewing area greater than the first viewing area. In still other features, the second viewing area includes a triangular area having rounded vertices with the first radius of curvature.

In other features, the shells receive the second plurality of blades and the actuator maintains the shells in the first position enclosing a third viewing area with a triangular area that is greater than the first viewing area.

In other features, the actuator positions the shells to a second position forming a fourth viewing area encompassed by the shells and planes extending from edges of adjacent shells, the fourth viewing area greater than the third viewing area. In still other features, the fourth viewing area includes a triangular area having rounded vertices with the second radius of curvature.

In other features, each proximal end of the shells includes a tapered portion to ease insertion over a dilator into surrounding tissue. In still other features, at least one of the first plurality of blades and the second plurality of blades includes decreasing radius of curvature at one edge to for nesting with adjacent blades.

A method for retracting tissue from a surgical area includes the steps of attaching a plurality of shells to a retractor, each of the plurality of shells having a rigid proximal end attached to each of the plurality of armatures and an opening, a distal closed end, and a pliable portion including a pocket in communication with the opening and extending along a length of the shell to the distal closed end; inserting a first plurality of retractor blades into the plurality of shells, each including a first geometry, each received through the opening into the pocket and shaping the pliable portion to configure the shells in a first configuration; and inserting a second plurality of retractor blades into the plurality of shells, each including a second geometry, each received through the opening into the pocket and shaping the pliable portion to configure the shells in a second configuration.

In other features, the first geometry includes a first radius of curvature in a plane normal to the length of the shell and the second configuration includes a second radius of curvature in the plane normal to the length of the shell that is greater than the first radius of curvature.

In other features, the method includes the step of removing at least one of the first plurality of blades before inserting one of the second plurality of blades. In still other features, the method includes the step of positioning the plurality of shells while in the first configuration to a first position and inserting the plurality of shells over a dilator. In yet other features, the method includes the step of positioning the plurality of shells while in the second configuration to a second position.

BRIEF DESCRIPTION OF THE DRAWINGS

FIGS. 6A-6D are a series of perspective views illustrating systems and methods according to the principles of the present disclosure.

FIGS. 7A-7D are a series of perspective views illustrating systems and methods according to the principles of the present disclosure.

DETAILED DESCRIPTION

Soft tissue retractor systems are used in minimally invasive spine fusion cases to provide direct access to the intervertebral space for disc extraction and interbody deliver. Generally, direct lateral approaches include insertion of a retractor system with three or more robust blades to split the psoas muscle and expand the retractor to pull away soft tissue from the surgical area to enable access by the surgeon. One issue during expansion of the retractor is soft tissue encroachment between the opened blades. This soft tissue reduces the field of view and may impede passage of instrumentation. Ideally, increasing the width of the blades reduces tissue encroachment. However, the width of the blades is limited by the need to nest the collapsed blade segments circumferentially around a dilator, typically in a cylindrical configuration. The blades must create a smooth exterior that can pass over the dilator and through the soft tissue with minimal effort.

To overcome the soft tissue encroachment, auxiliary blades and shims may be attached to the retractor and/or blades to fill some of the gaps between the blades. This increases the complexity and length of the procedure. Therefore, a means of increasing the blade width to improve soft tissue extraction is desirable to reduce the need for using auxiliary devices to supplement the retractor blades.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

Figure 1:
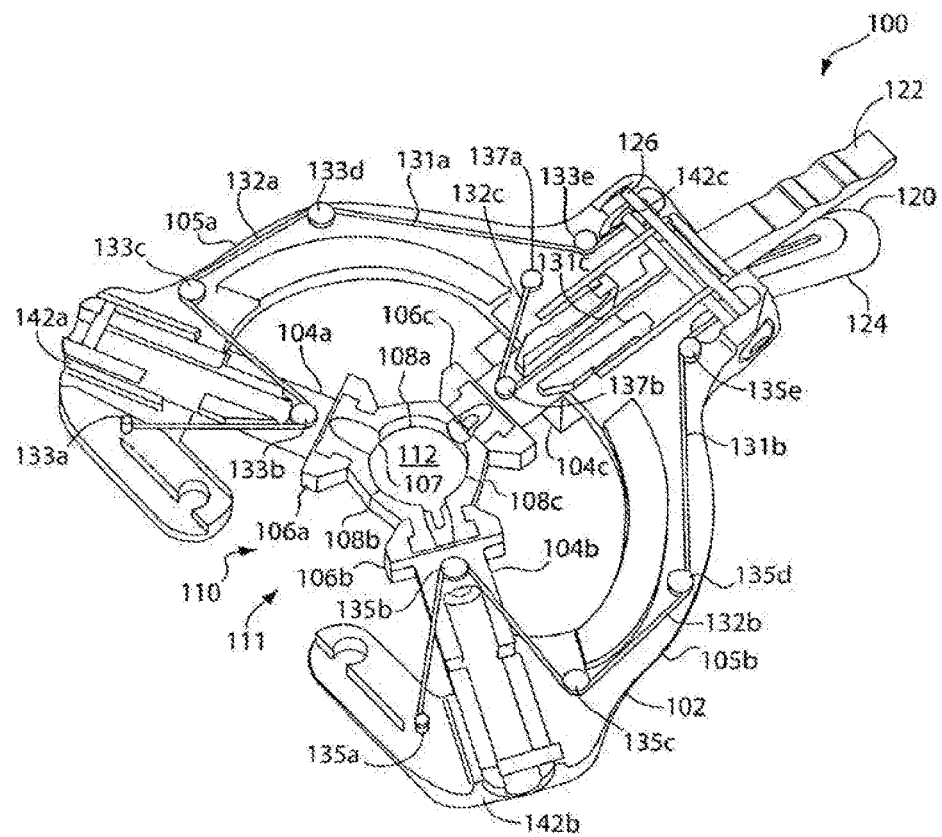
FIG. 1 is a perspective bottom view of an exemplary retractor for use with the systems and methods of tissue retraction according to the principles of the present disclosure.

FIG. 1 is a perspective, cross-sectional bottom view of a retractor device 100 which includes a housing 102, a handle assembly 120, three blade holders 104 (*a, b, c*), and three blades 108 (*a, b, c*). As can be understood by one skilled in the art, there can be any number of blade holders 104 and blades 108.

The housing 102 further includes a hollow interior or a halo 110 formed by the sides 105(a, b). The sides 105 (a, b) are joined together at the handle assembly 120 and form a gap 111 opposite the handle assembly 120. As can be understood by one skilled in the art, the sides 105 can be joined together at all times and not form any gaps. The hollow interior 110 further includes a center 112 that is located substantially in the center of the hollow interior 110.

As shown in FIG. 1, the blade holders 104 are configured to be slidably coupled to the housing 102, which allows the blade holders 104 to be capable of translational movement within the same plane as the plane of the housing 102. The movement of the blade holders 104 is configured to be within the hollow interior 110 and to and/or from (or away from) the center 112 (i.e., radially). The housing 102 further includes channels 142 (a, b, c) that are configured to hold the blade holders 104 and allow such translational movement of the blade holders 104. The channels 142 are further configured to be aligned in a direction of the center 112, thereby allowing blade holders 104's translational movement.

The handle assembly includes a permanent handle 124 and an actuating handle 122. The permanent handle 124 may be rigidly coupled to the housing 102. In one embodiment, the permanent handle 124 may be permanently coupled to the sides 105. The actuating handle 122 is pivotally coupled to a spool mechanism 126, which, in turn, may be coupled to the sides 105 and/or to the permanent handle 124. The spool mechanism 126 is configured to allow actuating handle 122 to at least partially pivot to and from the permanent handle 124. The handle assembly 120 is further configured to be coupled to a plurality of cable systems 131(a, b, c). The spool mechanism 126 can be a catch-and-release mechanism (e.g., ratchet type) that is configured to pull cables when the mechanism is actuated by a handle and release cables when the handle is released. This mechanism may include a spring-loaded device and a stopper device that allow pulling and releasing of the cables. As can be understood by one skilled in the art, other mechanisms and methods of pulling/tensioning and releasing the cables may be used.

The cable system 131a is configured to connect the handle assembly 120 and the first blade holder 104a. The cable system 131b is configured to connect the handle assembly 120 and the second blade holder 104b. The cable system 131c is configured to connect the handle assembly 120 and the third blade holder 104c.

The cable system 131a further includes a cable 132a and a plurality of pins 133 (a, b, c, d, e). The cable 132a is configured to be permanently secured to the pin 133a on the housing 105a as well as to be permanently secured to the spool mechanism 126 of the handle assembly 120. The cable 132a forms a sliding or a rolling connection with other pins 133 (b, c, d, e), including the pin 133b located on the blade holder 104a. The pins 133a, 133b, and 133c form a triangular composition that allows translational movement of the blade holder 104a. The pins 133d, 133e allow the cable 132a to be strung around the side 105a so as to prevent interference of the cable 132a with other components of the retractor device 100 as well as patient's body tissue which is selected for retraction.

The cable system 131b may further include a cable 132b and a plurality of pins 135 (a, b, c, d, e). The cable 132b is configured to be permanently secured to the pin 135a on the housing 105b as well as to be permanently secured to the spool mechanism 126 of the handle assembly 120. The cable 132b forms a sliding or a rolling connection with other pins 135 (b, c, d, e), including the pin 135b located on the blade holder 104b. The pins 135a, 135b, and 135c form a triangular composition that allows translational movement of the blade holder 104b. The pins 135d, 135e allow the cable 132b to be strung around the side 105b so as to prevent interference of the cable 132b with other components of the retractor device 100 as well as patient's body tissue which is selected for retraction.

The cable system 131c further includes a cable 132c and pins 137(a, b). The cable 132c may be configured to be permanently secured to the pin 137a on the housing 105a as well as to be permanently secured to the spool mechanism 126 of the handle assembly 120. The cable 132c forms a sliding or a rolling connection with pin 137b located on the blade holder 104c. The pins 137a and 137b form an angular composition that allows translational movement of the blade holder 104c. The pins 137a and 137b allow the cable 132c to be strung around the side 105a so as to prevent interference of the cable 132c with other components of the retractor device 100 as well as patient's body tissue which is selected for retraction.

As stated above, the cable systems 131 may be configured to allow translational movement of the blade holders 104, i.e., movement to and from the center 112 of the hollow interior 110. The blade holders 104 may be configured to be disposed within the housing in a triangular fashion. As can be understood by one skilled in the art, the blade holders 104 can be disposed in any other fashion, corresponding to the number and position of the blade holders used. To translate the blade holders 104 away from the center 112, the actuating handle 122 is forced towards the permanent handle 124 of the handle assembly 120 (i.e., squeezed). This causes cable systems 131 to tension and pull the cables 132 towards the spool mechanism 126. Once cable 132a is pulled, the triangular arrangement of pins 133 (a, b, c) forces the blade holder 104a to pull away radially from the center 112. Similarly, once the cable 132b is pulled, the triangular arrangement of pins 135(a, b, c) forces the blade holder 104b to radially pull away from the center 112. Also, once the cable 132c is pulled, the angular arrangement of pins 137(a, b) forces the blade holder 104c to radially pull away from the center 112. As can be understood by one skilled in the art, the pulling of each blade holder 104 can be simultaneous or selective (preferably, simultaneous). Further, the blade holders 104 can be pulled from the center 112 all the way to the sides 105 either in one application of forcing the handle 122 to the handle 124 or in several applications (i.e., gradually). The releasing of the blade holders 104 can be done in a similar fashion, but in a reverse order, i.e., releasing the handle 122 to release blade holders 104.

Blade holders 104(a, b, c)—which may also be referred to herein as armatures—may further include blade holder tips 106(a, b, c), respectively. Blade holder tips 106 are configured to couple the blade holders 104 to the blades 108. Thus, the blade holder tip 106a couples the blade holder 104a to the blade 108a; the blade holder tip 106b couples the blade holder 104b to the blade 108b; and the blade holder tip 106c couples the blade holder 104c to the blade 108c. In one embodiment, the blade holder tips 106 may be configured to receive blades 108 and secure the blades 108 inside the tips 106. The blade holder tips are further configured to allow doctors (or other qualified professionals) to exchange one set of blades 108 for another, if such exchange is desired. The blades 108 and the tips 106 can be frictionally fit together or a locking mechanism can be used to secure the blades 108 and the tips 106. In an alternate embodiment, the tips 106 and/or blade holders 104 can also be interchangeable, as desired.

As shown in FIG. 1, once the blade holders 104 are released, the blades 108 are pushed together towards the center 112. In the illustrated embodiments, the combination of the three released blades 108 forms a circle. As can be understood by one skilled in the art, the combination of the released blades can form any other shape, such as square, rectangle, polygon, oval, or any other regular or irregular shape. As can be further understood by one skilled in the art, there can be any number of blade holders 104, blade holder tips 106, and blades 108 coupled to the housing. The blades 108 along with corresponding holding mechanisms may be added or removed as desired. Also, the blades 108 can have any size shape, thickness, material or have any other parameters.

Figure 2:
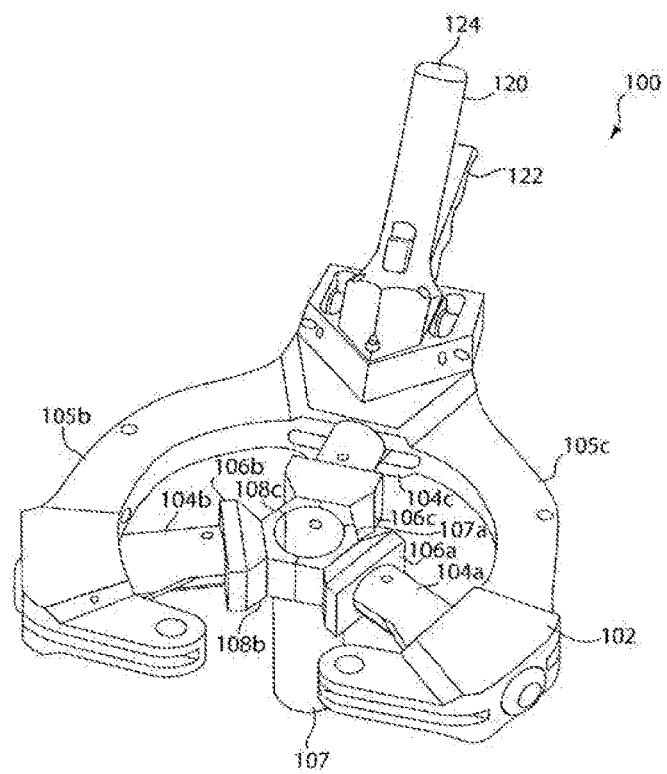
FIG. 2 is a perspective top view of the retractor of FIG. 1 according to the principles of the present disclosure.
Figure 3:
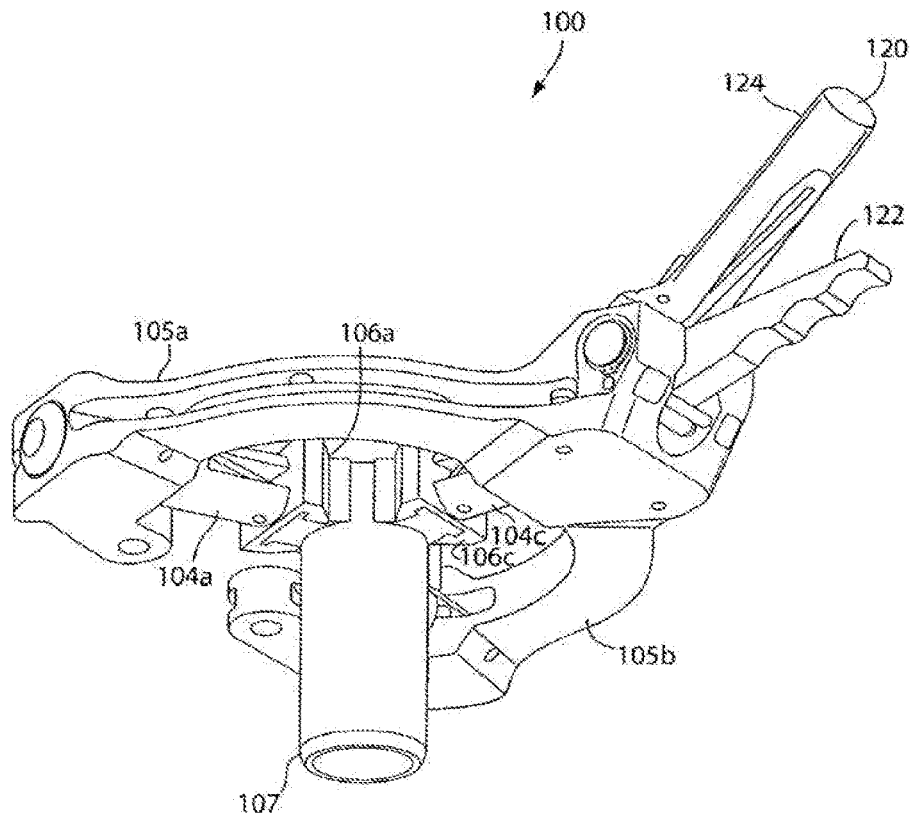
FIG. 3 is a perspective view of the back of the retractor of FIG. 1 according to the principles of the present disclosure.

Referring to FIGS. 2-3, the blades 108 can have any length, width, or shape. Specifically, FIG. 2, which is a top perspective view of the retractor 100, illustrates that the combination of released blades 108 forms a hexagon-shaped cylinder. Alternatively, FIG. 3, which is a bottom perspective view of the retractor 100, illustrates that the combination of released blades 108 forms a regular cylinder. As further illustrated in FIGS. 1-3, the sides 105(a, b) can be multi-layered, thereby allowing placement of cable systems 131 between the layers. This prevents interferences of the cable systems 131 during application of the retractor device 100 on the patient.

Figure 4:
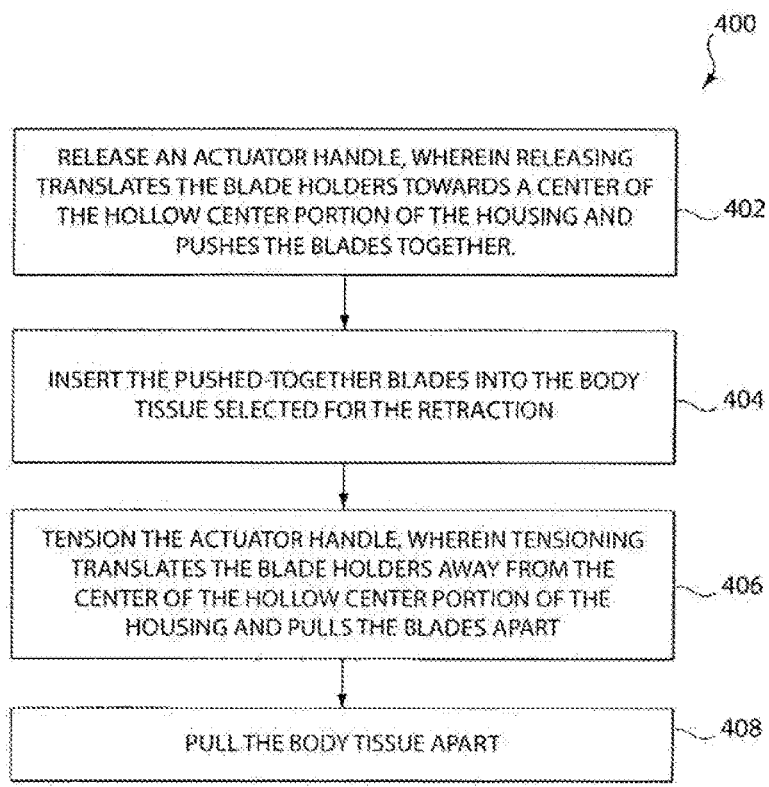
FIG. 4 is a flowchart of methods according to the principles of the present disclosure.

FIG. 4 illustrates a method 400 for retracting a body tissue within a body of a patient using a retractor device 100, illustrated in FIGS. 1-3. In step 402, the retractor blades 108 are released to allow the blades 108 to be pushed together towards the center 112 of the hollow center portion 110. In one embodiment, the step 402 is performed if the blades 108 are in a tensioned state, i.e., pulled away from the center 112.

In step 404, the retractor device 100, having blades 108 pushed together towards the center 112, is placed on the patient at a location where bodily tissue needs to be retracted. This location can be any location on or within the body, such as a location where a surgical procedure is being or will be performed. In an embodiment, the retractor device can be used to expose spinal structures during spinal surgery. This allows for minimal disruption of spinal muscles and sensitive elements of the posterior, lateral, and anterior regions of the spine. The retractor device 100 can also be used in the thoracolumbar region, as well as, sacral and cervical regions of the spine, or any other regions.

In step 406, the handle assembly 120 is used to tension the cables 132 of the cable systems 131. This may be accomplished be forcing the permanent handle 124 and the actuator handle 122 together (i.e., squeezing them together). Once the cables 132 are tensioned, the blade holders 104 slide or translate along the channels 142 away from the center 112 of the hollow portion 110. Once the blade holders 104 begin to slide, the blades 108 begin moving away from the center 112 as well and engage bodily tissue coming in contact with the blades 108. By forcing the blades 108 apart, the engaged bodily tissue are also spread/forced apart, as illustrated in step 408. As stated above, this exposes the bodily regions on which a surgical procedure may be performed. Also, by spreading the tissue apart, the surgeon (or other qualified professional) can easily move in and out any surgical tools needed for performing the surgical procedure.

As can be understood by one skilled in the art, the retractor device 100 and/or any of its components may have any size, shape, length, thickness, height, weight, or any other parameters. Such parameters may be selected by the surgeon (or other qualified professional) for performance of specific procedures. Further, the retractor device 100 and/or any of its components may be manufactured from metal, plastic, synthetic material, or other suitable materials, or any combination thereof.

Referring now to FIGS. 5-12, an exemplary system 200 for use with a retractor, such as retractor 100, includes features that enable insertion over a traditional dilator assembly and retractopm of soft tissue. The system 200 includes several components including shells 210 that receive retractor blades of various shapes. The shells 210 may include flexible or pliable portions. For example, the shells 210 may comprise various biocompatible plastics, braided mesh, or other material capable of altering shape to conform to various shaped blades. The shells 210 may be referred to as jackets, sleeves, or blade receptacles. In some examples, the blades of the present disclosure include a first plurality of blades 220 and second plurality of blades 230. The first blades 220 may include a first radius of curvature in the plane normal to the length of the blades. The second blades 230 may include a second radius of curvature in the plane normal to the length of the blades that is greater than the first radius. Alternately, one or more of the first blades 220 and the second blades 230 may include widths.

The shell 210 may be used in conjunction with the first blades 220 to insert the system 200 over a curved dilator, such as a cylindrical tube dilator. Once inserted, the first blades 220 may be removed and second blades 230 subsequently inserted. The second blades 230 may increase the diameter or area of the opening created by the retractor 100 over the first blades 220 by improving tissue retraction and preventing tissue encroachment into the surgical viewing area. The system 200 may include two or more of each component (shell, first blade, and second blade) as described herein. For ease of discussion, one of each of the components is described with reference to FIGS. 5A-5C.

Figure 5A:
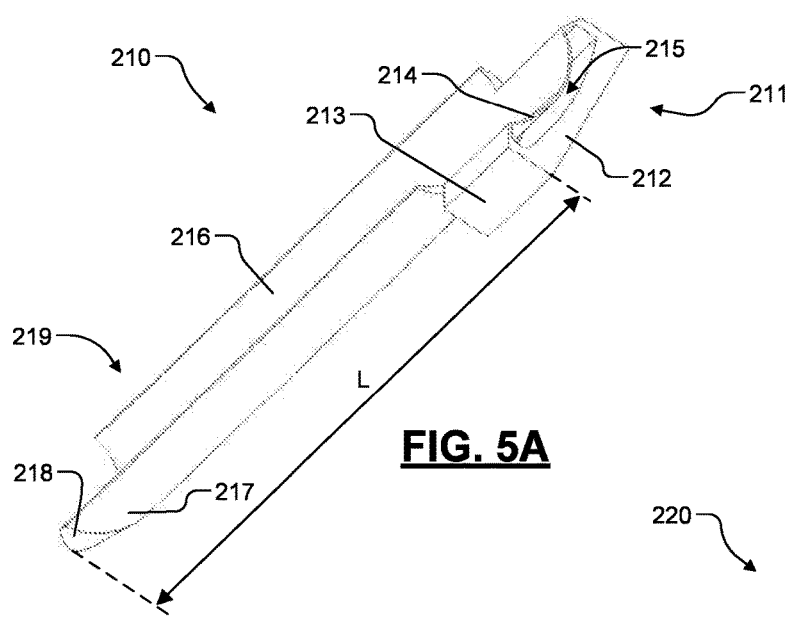
FIGS. 5A-5C are perspective views of various components of the system according to the principles of the present disclosure.

Referring now to FIG. 5A, the shell 210 includes a substantially slender profile extending a length L from a proximal end 211 to a distal end 219. Near the proximal end 211, a mount 212 for attachment to a retractor may include one or more attachment features and/or geometric features for removable coupling with the retractor. The mount 212 may include a boss 213 on the proximal end 211. The proximal end 211 may be more rigid than the distal end 219 to provide a strong connection with the retractor 100. The proximal end 211 further includes a proximal-facing opening 214 for receiving the various-shaped blades including the first blades 220 and second blades 230. The opening 214 may communicate with an interior pocket 215 extending within a blade-receiving portion 216 of the shell 210 to the distal end 219. The pocket 215 may bend, flex, expand, and conform to any of the blades 220 and 230. The distal end 219 may include a tapered portion 217 to ease insertion of the shell 210 over a dilator and into surrounding tissue. The distal end 219 may be closed. The shell 210 may include translucent tips 218 within the tapered portion 217 or along the length of the shell 210. The shell 210 may include various other pathway and/or connections for connecting instrumentation including probes, stimulators, and lighting.

Figure 5B:
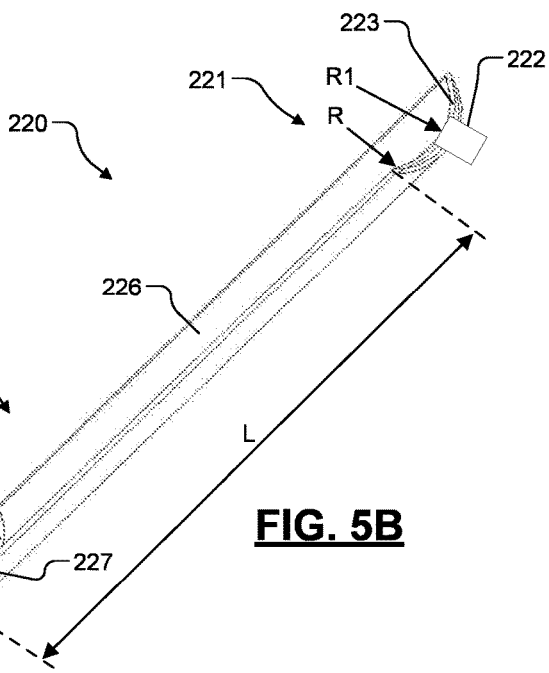

Referring now to FIG. 5B, the first blade 220 includes a substantially slender profile extending approximately length L from a proximal end 221 to a distal end 229. The proximal end 221 may include a tab 222 for inserting and removing the first blade 220 from the pocket 215. The first blade 220 may include various radii of curvature in a plane normal to the length L. The curvature may be substantially uniform or include decreasing or increasing radius at either end 221, 229 to enable nesting of multiple first blades 220 as describe herein. For example, near the middle of first blade edge 223, the radius may be R1 and near the end of the curved edge 223, the radius may be R. R1 may be greater than R. The curvature may be substantially uniform through a mid-portion 226 of the first blade 220. The first blade 220 may be substantially rigid and composed of hard plastic, metal, or other materials suitable for surgical use and capable of providing structure to the shell 210. The first blade 220 may include a tapered portion 227 near the distal end 229 to ease insertion into the pocket 215 of the shell 210. The first blade 220 may include various channels and pathways for instrumentation including probes, stimulators, and lighting.

Figure 5C:
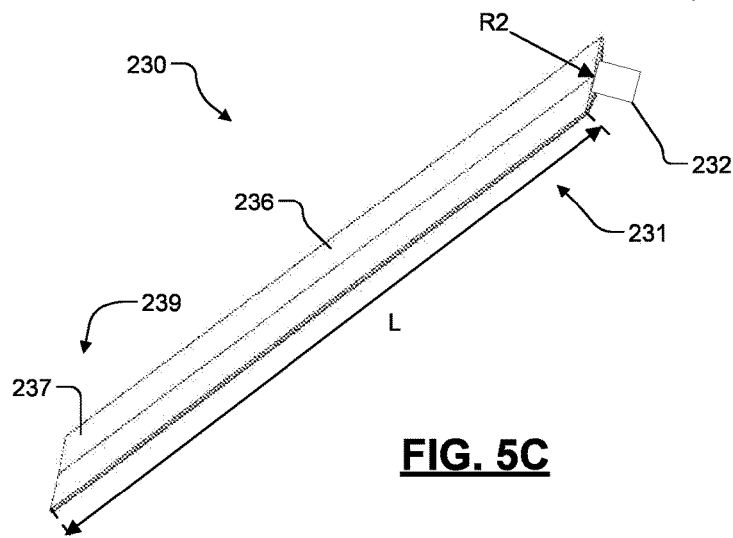

Referring now to FIG. 5C, the second blade 230 includes a substantially slender profile extending approximately length L form a proximal end 231 to a distal end 239. The proximal end 231 may include a tab 232 for inserting and removing the second blade 230 from the pocket 215. The second blade 230 may include a substantially flat profile with a radius of curvature R2 substantially greater than the radius of curvature R1 of the first blade 220. In some examples, the second radius of curvature R2 may be infinite as in the case of a flat, straight blade. The second blade 230, thus may include a width W. The curvature may be substantially uniform or include decreasing or increasing radius to enable nesting of multiple second blades 230 as describe above with respect to the first blade 220. The curvature may be substantially uniform through a mid-portion 236 of the second blade 230. The second blade 230 may be substantially rigid and composed of hard plastic, metal, or other materials suitable for surgical use. The second blade 230 may include a tapered portion 237 near the distal end 239 to ease insertion into the pocket 215 of the shell 210. The second blade 230 may include various channels and pathways for instrumentation including probes, stimulators, and lighting.

Referring now to FIGS. 6A-6D and 7A-7D, multiple shells 210, first blades 220, and second blades 230 may be used to insert the system 200 in a minimally invasive surgery (MIS) procedure. The system 200 may be used with one or more cylindrical dilators (not shown) that are first inserted into a patient to create a MIS pathway. For example, a series of increasing diameter dilators may be inserted into a patient as is known in the art until a final dilator remains. They system 200 may be coupled with the retractor 100 to position the shells 210.

In FIG. 6A, three shells 210a, 210b, and 210c (collectively shells 210) are assembled together (such as through attachment to a retractor) in a circular pattern to form generally system 200 with a proximal end 201 and a distal end 209. The proximal end 201 of the system 200 may be inserted over a final dilator. For example, the final dilator may include a diameter slightly less than or substantially equal to a diameter D of an opening 202 formed by the shells 210 of the tubular system 200. The opening 202 may be substantially circular at the proximal end 201 and extend the length L of the shells 210 to the distal end 209. At the distal end 209, the opening 202 may decrease slightly.

In FIG. 6B, three first blades 220a, 220b, and 220c (collectively first blades 220) may be inserted into respective shells 210a, 210b, and 210c of the system 200 to provide strength and rigidity for insertion over the final dilator. Each of the first blades 220 may be inserted into respective proximal facing openings 214a, 214b, and 214c. Continuing with FIG. 6C, the first blades 220 may be advanced distally into the respective pockets 215a, 215b, and 215c (none of which are shown) of the shells 210. As the first blades 220 advance, the blade receiving portions 216a, 216b, and 216c (not shown) of the shells 210 become more rigid to conform to the shape of the first blades 220. In FIG. 6D, the first blades 220 have completely advanced into the distal ends 219 of the shells 210 to form a substantially rigid tubular system 200 with rigid opening 202 extending from the proximal end 201 to the distal end 209.

In FIG. 7A, the rigid tubular system 200 has been inserted over the final dilator using the first blades 220. Each of the first blades 220 has been removed. The final dilator may be removed or left within the opening 202. The three shells 210a, 210b, and 210c may remain together in a circular pattern to form generally a tubular system 200 with the proximal end 201 and the distal end 209. For example, upon removal of the first blades 220, each of the shells 210 may become pliable again. In some examples, each of the first blades 220 may be removed one at a time and subsequently replaced one at a time by each of the second blades 230. In this manner, the system 200 may become partially pliable and partially rigid until all first blades 220 have been swapped out for second blades 230.

In FIG. 7A, three second blades 230a, 230b, and 230c (collectively second blades 230) may be inserted into respective shells 210 of the system 200 to provide strength and rigidity for retraction of tissue and improved prevention of encroachment of tissue. Each of the second blades 230 may be inserted into respective proximal facing openings 214a, 214b, and 214c. Continuing with FIG. 7B, the second blades 230 may be advanced distally into the respective pockets 215a, 215b, and 215c (none shown) of the shells 210. As the second blades 230 advance, the blade receiving portions 216a, 216b, and 216c (not shown) of the shells 210 become more rigid to conform to the shape of the second blades 230. In FIG. 7C, the second blades 230 have completely advanced into the distal ends 219 of the shells 210 to form a substantially rigid triangular system 200 with a triangular opening 202 extending from the proximal end 201 to the distal end 209. Referring now to FIG. 7D, the triangular opening 202 may be retracted using a retractor instrument such as the instrument 100 described herein. Any suitable instrument with the ability to position each shell 210 relative to one another may be used to retract the tissue.

Figure 8C:
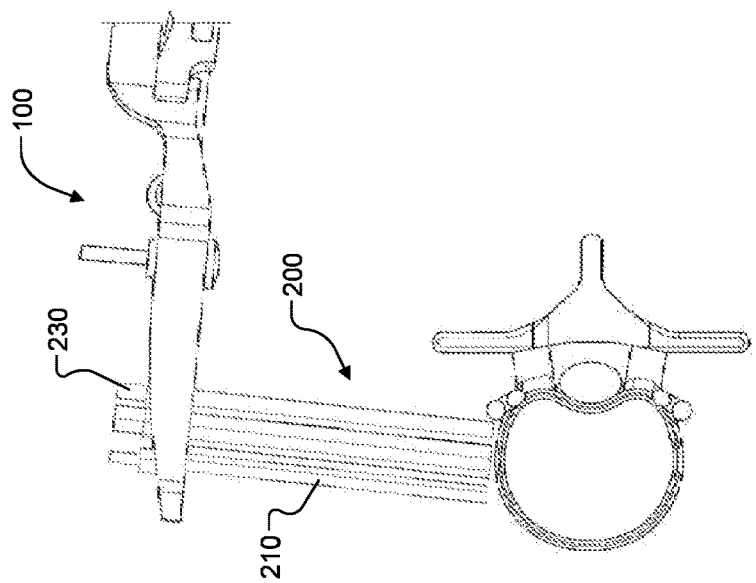
FIGS. 8A-8C are a series of side views illustrating systems and methods according to the principles of the present disclosure.
Figure 8B:
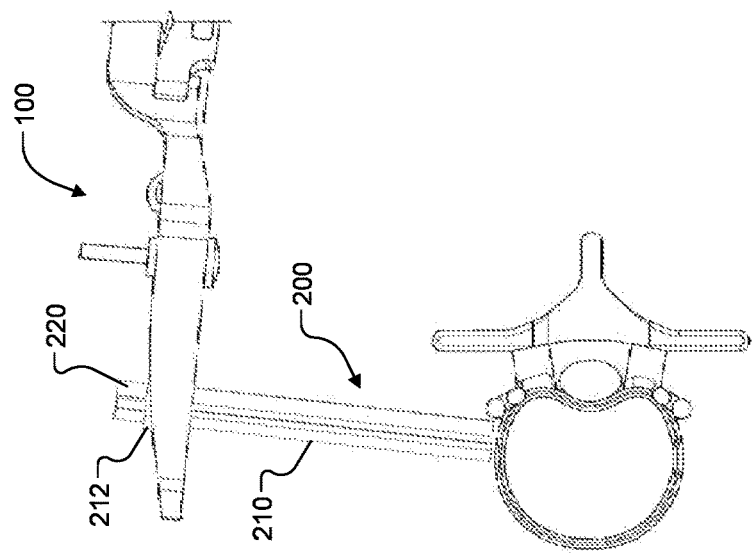
Figure 8A:
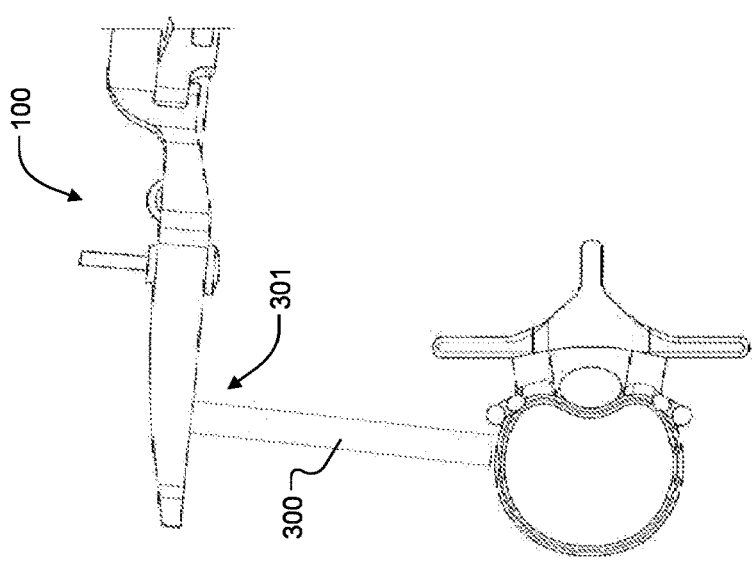

FIGS. 8A-8C illustrate exemplary steps of a method of using a retractor instrument 100, dilators 300, and system 200 of the present disclosure. In FIG. 8A, a patient may be positioned such that the side of the body is facing the surgeon. The surgeon may make an incision into the body to begin to access the spinal column and intervertebral disc space between two adjacent vertebrae. As shown in FIGS. 8A-8C, the surgeon may access a lumbar region of the spinal column. The surgeon may insert a series of concentric dilators as is known generally in the art of minimally invasive surgery (MIS) procedures until a final dilator 300 has been inserted. The retractor instrument 100 may be positioned over a proximal end 301 of the dilator 300 to receive the system 200 as described herein.

In FIG. 8B, the system 200 has been inserted over the dilator 300 using the first blades 220. The first blades 220 reinforce the pliable portions of the shells 210 of the system 200 as the shells 210 advance distally into the tissue of the patient. Once the shells 210 have advanced far enough into the tissue, the mounts 212 of the shells 210 may be attached to various armatures and mounting brackets of the instrument 100 to retain the generally tubular shape of the opening 202 at the proximal end 201 of the system 200. The dilator 300 may be removed or may remain in the tissue. Subsequently, the second blades 230 may be inserted into the shells 210 to form the triangular system 200. In FIG. 8C, the triangular system 200 may be used to retract tissue and create a wider opening than can be obtained using the first blades 220 as shown below with respect to FIGS. 9A-11.

FIGS. 9A-11 provide several views looking into the distal end of the system 200 with first blades 220 and second blades 230 inserted into the shells 210. For example, in FIG. 9A, the first blades 220 have been inserted into the shells 210 of the system 200. The first blades 220 within the shells 210 cause the system 200 to become more rigid as shown in FIGS. 6A-6D. The shells 210 form the generally rigid circular opening 202 extending from the proximal end 201 to the distal end 209. The opening 202 may include diameter D1 with a first viewing area A1. The first viewing area A1 may be substantially a circular area.

Figure 9A:
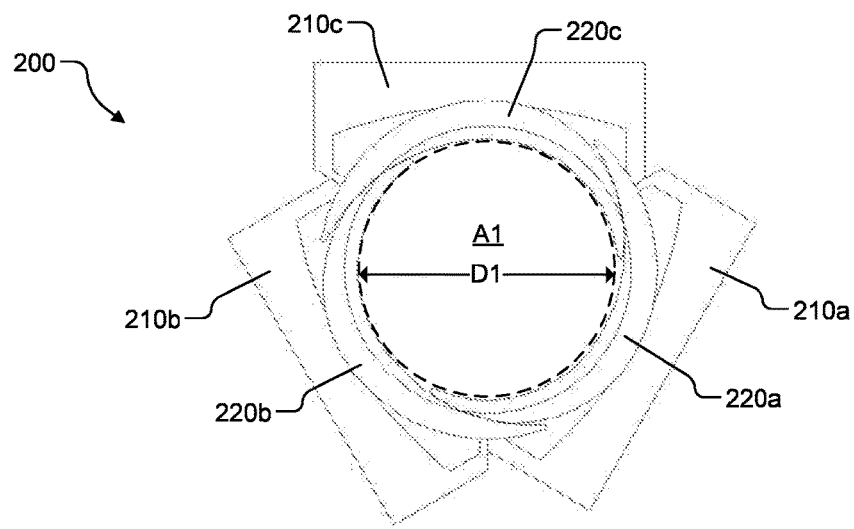
FIGS. 9A and 9B are distal views of the system in a first configuration of the present disclosure in an insertion position and a retracted position.
Figure 9B:
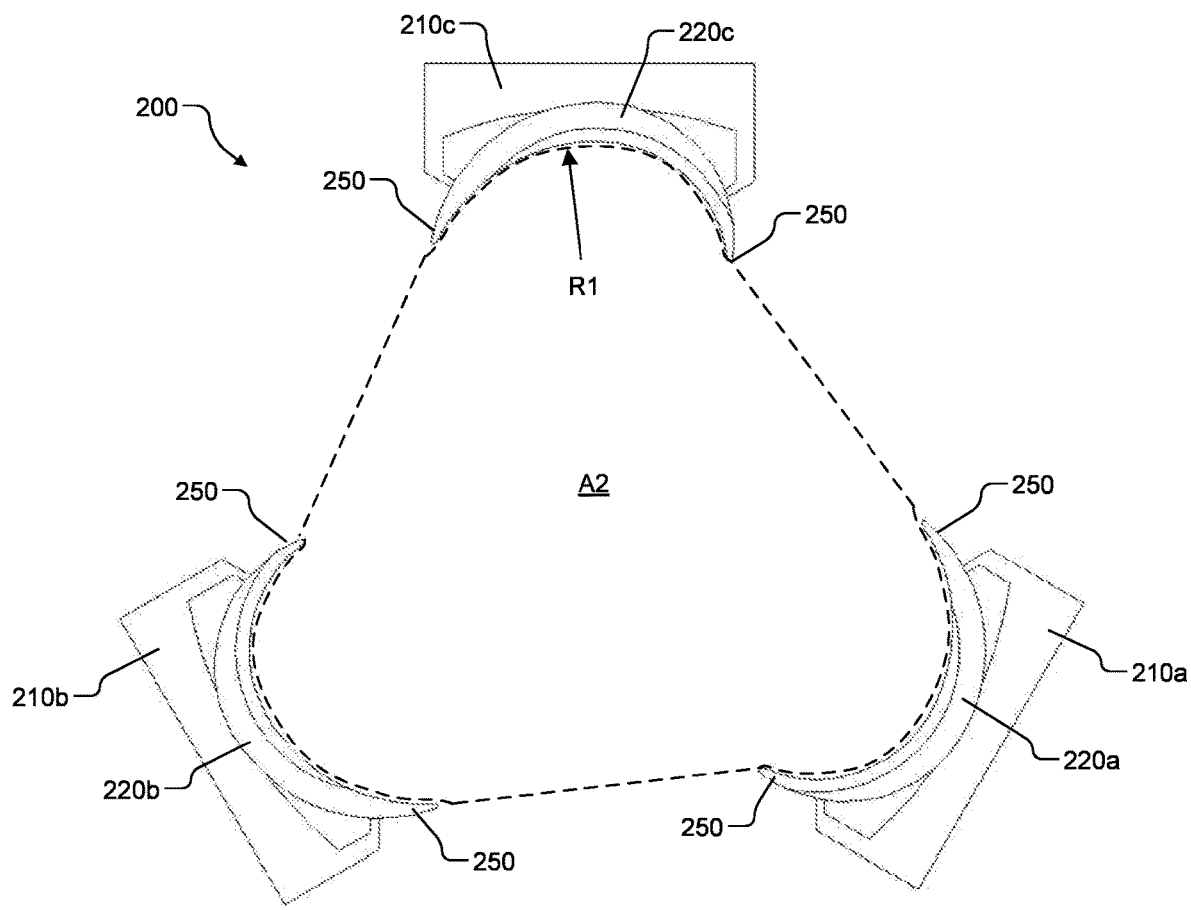

The system 200 may be used to retract tissue using the first blades 220 as shown in FIG. 9B. As the shells 210 with the first blades 220 spread apart, the opening 202 increases in size to a second viewing area A2. The second viewing area A2 may include a substantially triangular area with curved vertices (due to the radius of curvature R1 of the first blades 220) formed by the shells 210 and imaginary planes extending from adjacent edges 250 of the shells 210 as represented by dotted lines. In practice, soft tissue may encroach past the imaginary planes somewhat.

However, the second viewing area A2 may be increased by using the second blades 230 in place of the first blades 220. For example, the first blades 220 may be removed after insertion over the final dilator as described above. The second blades 230 may then be inserted into the shells 210.

Figure 10A:
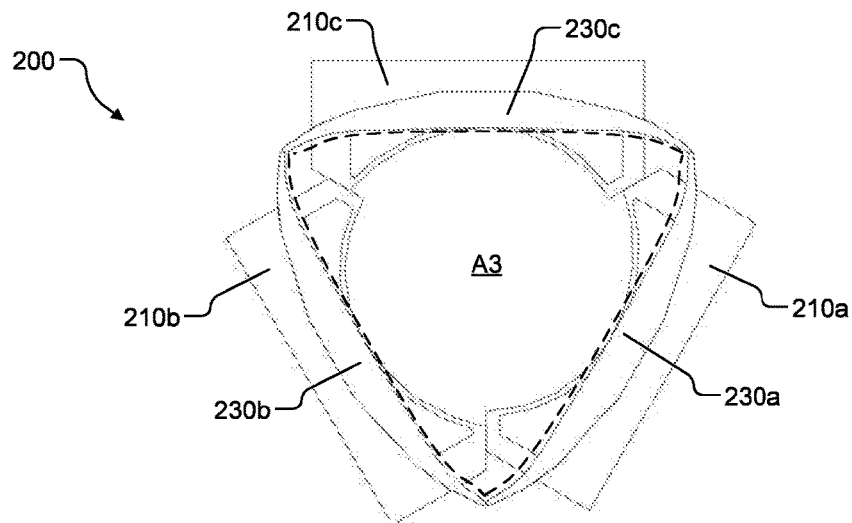
FIGS. 10A and 10B are distal views of the system in a second configuration of the present disclosure in an insertion position and a retracted position.

In FIG. 10A, the second blades 230 have been inserted into the shells 210 of the system 200 after removal of the first blades 220. The second blades 230 within the shells 210 cause the system 200 to become more rigid as shown in FIGS. 7A-7D. The shells 210 form the generally triangular opening 202 extending from the proximal end 201 to the distal end 209. The opening 202 may include three sides of width W corresponding to the shells 210 that form a generally triangular third viewing area A3. The third viewing area A3 may be greater than the first viewing area A1.

Figure 10B:
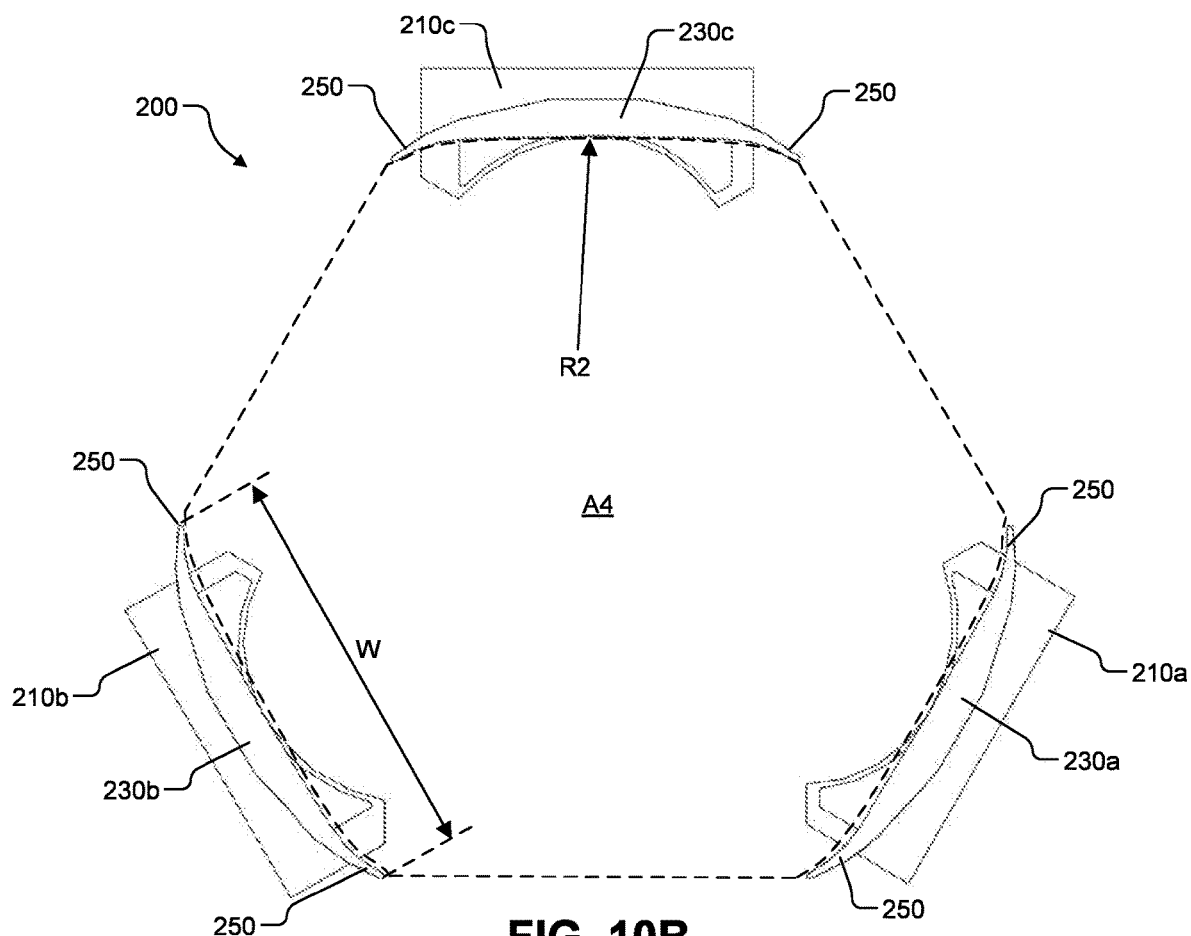

The system 200 may then be used to retract tissue using the second blades 230 as shown in FIG. 10B. As the shells 210 with the second blades 230 spread apart, the opening 202 increases in size to a fourth viewing area A4 that is substantially greater than the second viewing area A2 formed using the first blades 220. Like the second and third viewing areas A2 and A3, the fourth viewing area A4 may include a substantially triangular area with flattened vertices having width W (due to the radius of curvature R2 or width W of the second blades 220) formed by the shells 210 and planes extending from the adjacent edges 250 of the shells 210 as represented by the dotted lines.

Figure 11:
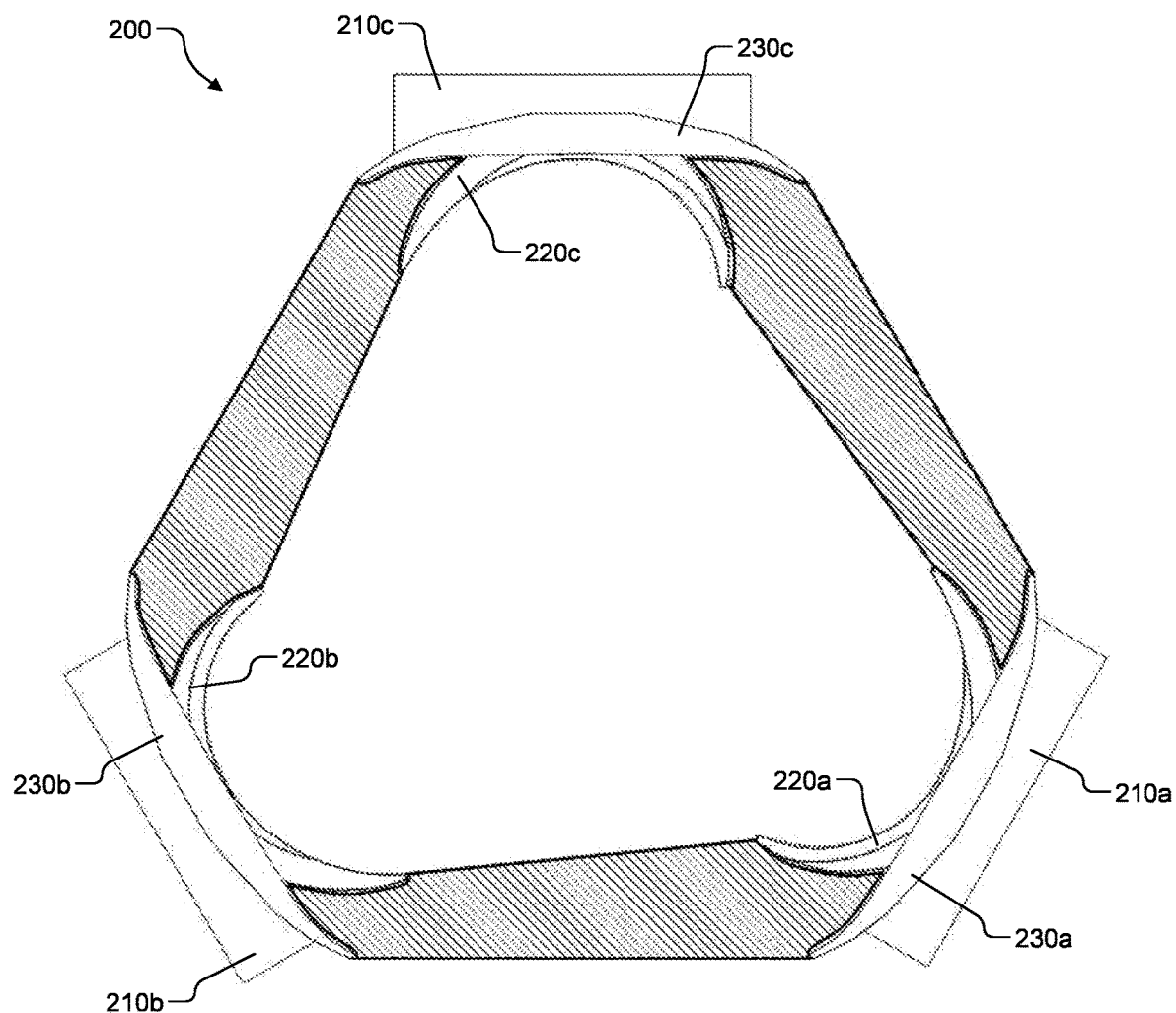
FIG. 11 is a distal view illustrating the difference in size of surgical viewing areas of the system in the first configuration and second configuration when in the retracted positions.

As shown in FIG. 11, the second blades 230 provide a greater area of retraction than using the first blades 220. Shaded areas represent the additional area retracted using the second blades 230 over the first blades 220.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. A system for interchangeable retractor blades, comprising:
   a shell having an opening at a proximal end, the proximal end configured to attach to a surgical retractor, a distal end, and a pliable portion including a pocket in communication with the opening and extending toward the distal end;
   a first retractor blade having a first geometry, the first retractor blade configured to be received into the pocket through the opening; and
   a second retractor blade having a second geometry different from the first geometry, the second retractor blade configured to be received into the pocket through the opening.

2. The system of claim 1, wherein the first geometry is defined by a first radius curvature in a plane normal to a length of the shell.

3. The system of claim 2, wherein the second geometry is defined by a second radius of curvature in the plane normal to a length of the shell that is greater than the first radius of curvature.

4. The system of claim 1, wherein the first retractor blade has a length commensurate with a length of the shell, an overall thickness configured to slidably engage with the pocket, and a curved profile commensurate with a curvature of the shell in a plane normal to the length of the first retractor blade.

5. The system of claim 4, wherein the second retractor blade has a length commensurate with the length of the shell, an overall thickness configured to slidably engage with the pocket, and a straight profile configured to decrease the curvature of the shell in the plane normal to the length of the second retractor blade.

6. A system for retracting tissue from a surgical area, comprising:
   a retractor including an actuator that positions a plurality of armatures;
   a plurality of shells each having a proximal end, a distal end, a pliable portion between the proximal and distal ends, an opening near the proximal end, the opening connecting to a pocket extending from the proximal end, the proximal end being configured to be attached to each of the plurality of armatures;
   a first plurality of retractor blades, each having a first geometry, each being configured to be received into the pocket through the opening; and
   a second plurality of retractor blades, each having a second geometry different from the first geometry, each being configured to be received into the pocket through the opening.

7. The system of claim 6, wherein the first geometry is defined by a first radius curvature in a plane normal to a length of the shell and the second geometry is defined by a second radius of curvature in the plane normal to the length of the shell, the second radius of curvature being greater than the first radius of curvature.

8. The system of claim 7, wherein the shells receive the first plurality of blades, and the actuator is configured to position the shells in a first position enclosing a first viewing area with a circular area of a first diameter.

9. The system of claim 8, wherein the actuator is configured to move the shells from the first position to a second position forming a second viewing area encompassed by the shells and planes extending from edges of adjacent shells, the second viewing area being larger in size than the first viewing area.

10. The system of claim 9, wherein the second viewing area includes a triangular area having rounded vertices with the first radius of curvature.

11. The system of claim 8, wherein the shells are configured to receive the second plurality of blades and the actuator is configured to maintain the shells in the first position enclosing a third viewing area with a triangular area that is larger in size than the first viewing area.

12. The system of claim 11, wherein the actuator is configured to move the shells from the first position to a second position forming a fourth viewing area encompassed by the shells and planes extending from edges of adjacent shells, the fourth viewing area being larger in size than the third viewing area.

13. The system of claim 12, wherein the fourth viewing area is defined by a triangular area having rounded vertices with the second radius of curvature.

14. The system of claim 11, wherein each proximal end of the shells includes a tapered portion to ease insertion over a dilator into surrounding tissue.

15. The system of claim 11, wherein at least one of the first plurality of blades and the second plurality of blades includes a decreasing radius of curvature at one edge for nesting with adjacent blades.

16. A method for retracting tissue from a surgical area, comprising:
attaching a plurality of shells to a retractor, each of the plurality of shells having a proximal end, a distal end, an opening near the proximal end that leads to a pocket extending from the proximal end, the proximal end of each shell configured to attach to each of a plurality of armatures on the retractor;
inserting a first plurality of retractor blades into the plurality of shells, each having a first geometry and configured to be received through the opening into the pocket;
inserting a second plurality of retractor blades into the plurality of shells, each having a second geometry different from the first geometry and configured to be received through the opening into the pocket.

17. The method of claim 16, wherein the first geometry includes a first radius curvature in a plane normal to a length of the shell and the second geometry includes a second radius of curvature in the plane normal to the length of the shell, the second radius of curvature being greater than the first radius of curvature.

18. The method of claim 17, further comprising the step of removing at least one of the first plurality of blades before inserting one of the second plurality of blades.

19. The method of claim 16, further comprising positioning the plurality of shells in a first position and, while in the first position, inserting the plurality of shells over a dilator.

20. The method of claim 19, further comprising repositioning the plurality of shells to a second position.

* * * * *